US010201381B2

(12) United States Patent
Zergiebel et al.

(10) Patent No.: US 10,201,381 B2
(45) Date of Patent: Feb. 12, 2019

(54) HAND INSTRUMENTS WITH SHAPED SHAFTS FOR USE IN LAPAROSCOPIC SURGERY

(71) Applicant: SurgiQuest, Inc., Milford, CT (US)

(72) Inventors: Earl M. Zergiebel, Guilford, CT (US); Dominick Mastri, Bridgeport, CT (US); Michael J. Augelli, Prospect, CT (US); Kurt Azarbarzin, Fairfield, CT (US)

(73) Assignee: Conmed Corporation, Utica, NY (US)

( * ) Notice: Subject to any disclaimer, the term of this patent is extended or adjusted under 35 U.S.C. 154(b) by 440 days.

(21) Appl. No.: 14/736,364

(22) Filed: Jun. 11, 2015

(65) Prior Publication Data

US 2016/0361107 A1    Dec. 15, 2016

(51) Int. Cl.
*A61B 17/29* (2006.01)
*A61B 18/08* (2006.01)
*A61B 18/14* (2006.01)

(52) U.S. Cl.
CPC ............ *A61B 18/085* (2013.01); *A61B 17/29* (2013.01); *A61B 18/1445* (2013.01); *A61B 2017/2901* (2013.01); *A61B 2017/293* (2013.01); *A61B 2017/2906* (2013.01); *A61B 2017/2912* (2013.01); *A61B 2017/2933* (2013.01);
(Continued)

(58) Field of Classification Search
None
See application file for complete search history.

(56) References Cited

U.S. PATENT DOCUMENTS

| 5,381,788 A | 1/1995 | Matula et al. |
| 5,391,180 A | 2/1995 | Tovey et al. |
| 5,411,519 A | 5/1995 | Tovey et al. |

(Continued)

FOREIGN PATENT DOCUMENTS

| EP | 2659848 A2 | 11/2013 |
| EP | 2687177 A2 | 1/2014 |

(Continued)

OTHER PUBLICATIONS

Partial International Search Report dated Jun. 30, 2016 in connection with PCT/US2016/028900.

(Continued)

*Primary Examiner* — Erica S Lee
(74) *Attorney, Agent, or Firm* — Locke Lord LLP; Scott D. Wofsy

(57) ABSTRACT

A surgical instrument for use in laparoscopic surgical procedures is disclosed that includes an elongated shaped outer shaft having opposed proximal and distal end portions, and having a non-circular cross-sectional profile, an end effector operatively associated with a distal end portion of the shaped outer shaft and including a pair of cooperating jaw members configured for movement between open and closed positions, a proximal handle assembly operatively associated with a proximal end portion of the shaped outer shaft and including a pivoting actuation handle, and an elongated actuation member extending through the shaped outer shaft from the proximal handle assembly to the end effector, whereby movement of the actuation handle causes corresponding movement of the cooperating jaw members.

31 Claims, 16 Drawing Sheets

(52) U.S. Cl.
CPC ............... *A61B 2017/2939* (2013.01); *A61B 2017/2948* (2013.01)

(56) References Cited

U.S. PATENT DOCUMENTS

| | | | |
|---|---|---|---|
| 5,485,952 | A | 1/1996 | Fontayne |
| 5,514,157 | A * | 5/1996 | Nicholas ............ A61B 17/0218 600/201 |
| 8,795,223 | B2 | 8/2014 | Stearns et al. |
| 2004/0193212 | A1 | 9/2004 | Taniguchi et al. |
| 2010/0298824 | A1* | 11/2010 | Rothstein ............ A61B 18/1445 606/41 |
| 2012/0022525 | A1 | 1/2012 | Dietz et al. |
| 2012/0078248 | A1* | 3/2012 | Worrell .............. A61B 18/1445 606/45 |
| 2013/0030428 | A1 | 1/2013 | Worrell et al. |
| 2015/0105820 | A1 | 4/2015 | Fan et al. |
| 2016/0338763 | A1* | 11/2016 | Allen, IV ........... A61B 18/1445 |

FOREIGN PATENT DOCUMENTS

| | | |
|---|---|---|
| WO | WO-2012006306 A2 | 1/2012 |
| WO | WO-2013009699 A2 | 1/2013 |

OTHER PUBLICATIONS

International Search Report and Written Opinion for PCT Application No. PCT/US2016/028900, dated Sep. 19, 2016.

* cited by examiner

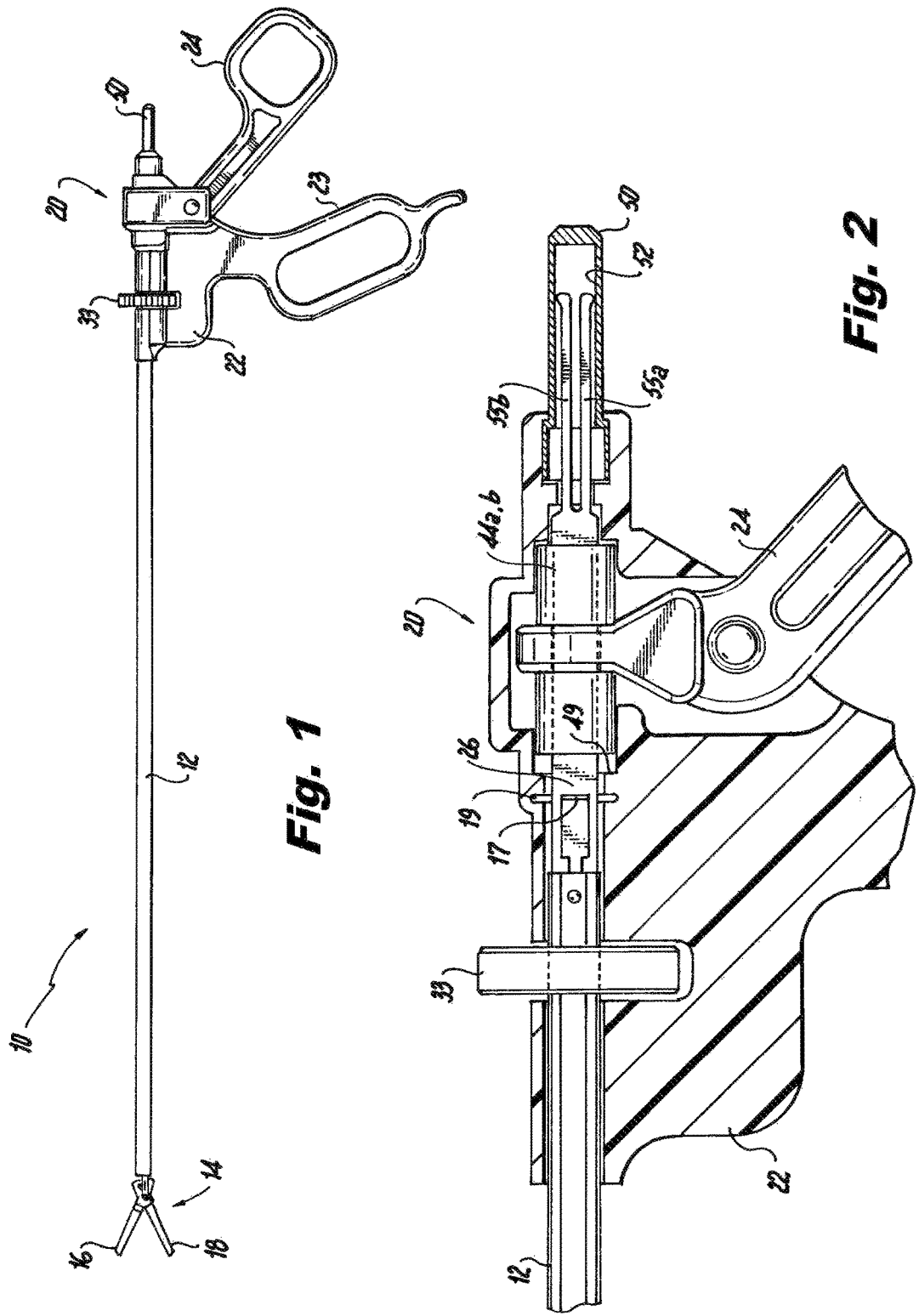

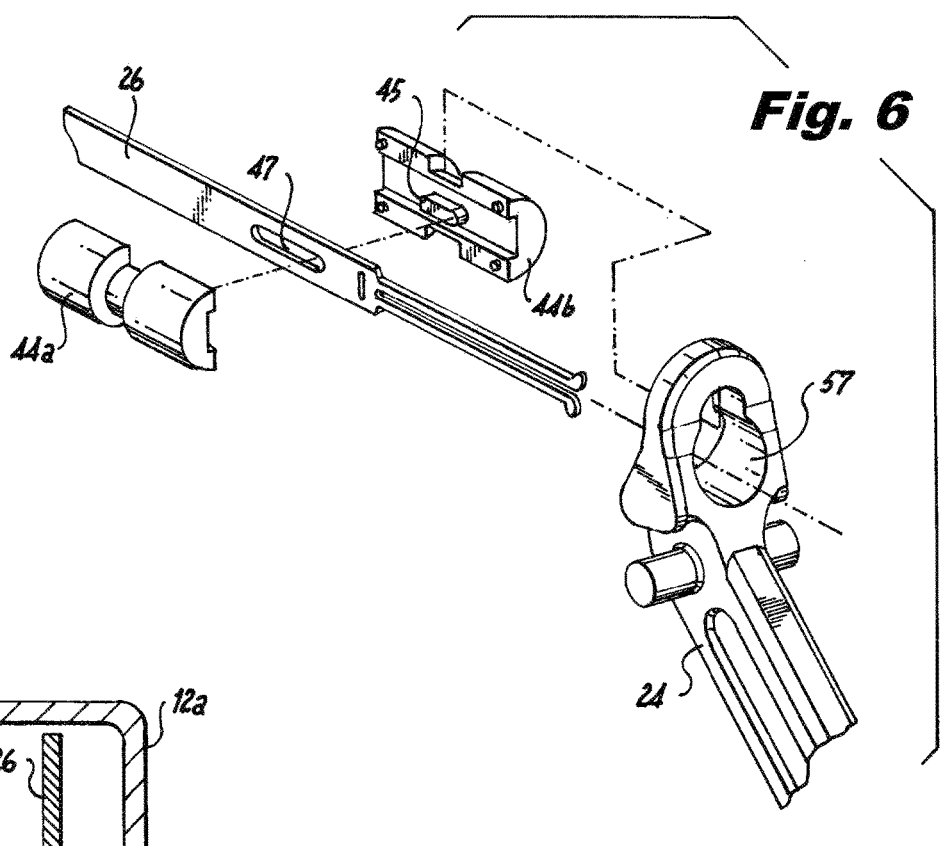
Fig. 6
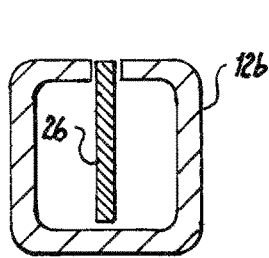
Fig. 7
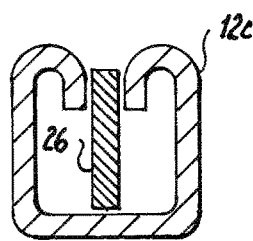
Fig. 8
Fig. 9
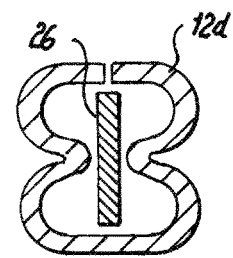
Fig. 10

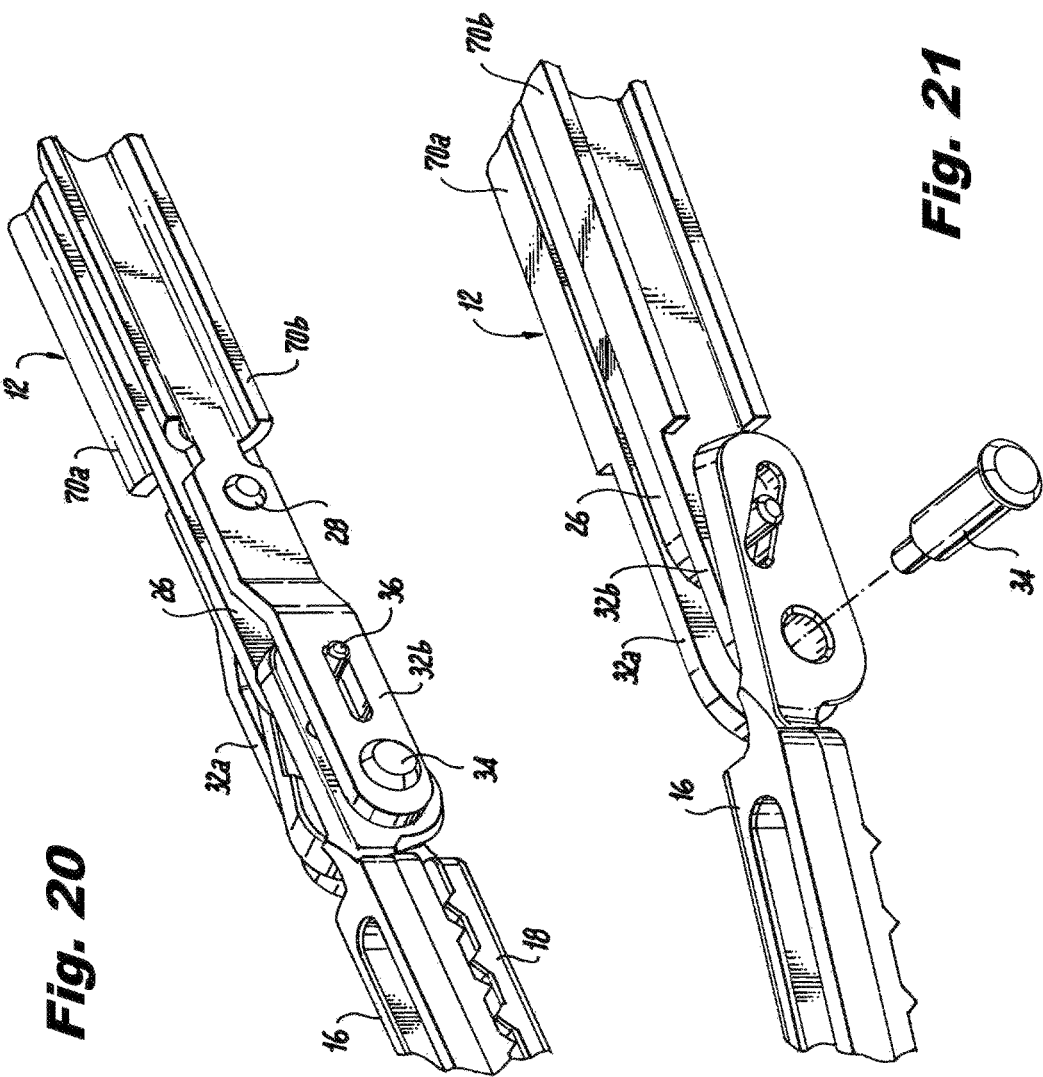

HAND INSTRUMENTS WITH SHAPED SHAFTS FOR USE IN LAPAROSCOPIC SURGERY

BACKGROUND OF THE INVENTION

1. Field of the Invention

The subject invention is directed to surgical instrumentation, and more particularly, to hand instruments with shaped shafts for use in laparoscopic surgery performed through pneumatically sealed trocars, rather than conventional mechanically sealed trocars, and method of making such instruments.

2. Description of Related Art

Hand instruments for use in laparoscopic surgical procedures are well known in the surgical arts. They are typically constructed with an end effector provided at the distal end of an elongated shaft that is controlled by an actuation handle associated with the proximal end of the shaft. The end effector is designed to perform a certain surgical task such as, for example, cutting, grasping, ligating or retracting.

It is conventional for the shaft of a laparoscopic surgical instrument to be circular in cross-section. This is so the periphery of the instrument shaft can be effectively sealed within the tubular trocar sleeve through which it passes in order to gain access to the abdominal cavity of a patient during a laparoscopic surgical procedure. When a trocar having a pneumatic sealing system is employed, such as that which is disclosed in commonly assigned U.S. Pat. No. 8,795,223, the instrument shaft does not need to be formed in a conventional manner. That is, the instrument shaft need not have a circular-cross-section. This opens up the design envelope for laparoscopic instruments, allowing for differently shaped, non-circular shafts and manufacturing methods that are not currently used in the surgical art.

SUMMARY OF THE INVENTION

The subject invention is directed to a surgical instrument for use in laparoscopic surgical procedures that are performed through pneumatically sealed trocars as opposed to conventional mechanically sealed trocars. The surgical instruments of the subject invention include an elongated shaped outer shaft having opposed proximal and distal end portions, and a non-circular cross-sectional profile.

An end effector is operatively associated with a distal end portion of the elongated outer shaft. The end effector includes a pair of cooperating jaw members configured for movement between open and closed positions. The instrument includes a proximal handle assembly having a barrel portion aligned with the shaped outer shaft, a stationary handle depending from the barrel portion, and a pivoting actuation handle that moves relative to the stationary handle. An elongated actuation member or ram shaft extends through the shaped outer shaft of the instrument from the proximal handle assembly to the end effector. In operation, movement of the pivoting actuation handle causes corresponding movement of the cooperating jaw members between open and closed positions.

The distal end portion of the elongated actuation member is operatively connected to the outer shaft by a transverse guide pin that resides within a linear guide slot formed in the actuation member. The distal end portion of the outer shaft includes a bifurcated yoke section having a pair of parallel yoke arms for accommodating the cooperating jaw members of the end effector. In one embodiment of the invention, the cooperating jaw members are located inside of or otherwise between the two parallel arms of the bifurcated yoke section. In another embodiment, the cooperating jaw members are located outside of the bifurcated yoke section, while the actuation member extends between the two arms of the yoke section.

A distal end portion of the actuation member is operatively connected to the cooperating jaw members of the end effector by a transverse cam pin. The transverse cam pin travels within linear slots formed in the arms of the bifurcated yoke section of the outer shaft and within an angled cam slot formed in the base of each jaw member.

In one embodiment of the subject invention, a proximal end portion of the actuation shaft includes a generally cylindrical coupling for operatively connecting the actuation member or ram shaft to the pivoting actuation handle. In another embodiment of the subject invention, a proximal end portion of the actuation shaft includes a pair of spaced apart flexible tabs for operatively connecting the actuation shaft to the pivoting actuation handle. Preferably, the proximal end portion of the actuation shaft is cooperatively connected to an electrical contact pin or banana plug to facilitate the performance of electro-cautery procedures.

In one embodiment of the invention, the outer shaft has a beam shaped configuration that includes a transverse web section. In such an instance, the actuation member or ram shaft includes a longitudinal slot for accommodating the transverse web section of the outer shaft. The shaped outer shaft has a beam-shaped cross-sectional configuration that includes opposed concave lateral supports for added structural strength and rigidity. In one instance, the opposed concave lateral supports have a generally rectangular configuration. In another instance, the opposed concave lateral supports have a generally rounded configuration.

The subject invention is also directed to an articulating surgical instrument for use in laparoscopic surgical procedures. The instrument includes an elongated shaped outer instrument shaft having a non-circular cross-sectional profile. The instrument further includes an articulation coupler operatively associated with a distal end portion of the outer instrument shaft. The articulation coupler has a central axis and is mounted for articulated angular movement relative to a longitudinal axis of the elongated outer shaft. A yoke assembly or rotational coupler is operatively associated with the articulation coupler, and an end effector is operatively associated with the yoke assembly. The yoke assembly or rotational coupler is mounted for axial rotation relative to the articulation coupler. The end effector includes a pair of cooperating jaw members that are configured for movement between open and closed positions.

The articulating surgical instrument further includes a proximal handle assembly having an elongated barrel portion aligned with the shaped outer shaft, a stationary handle depending from the barrel portion and a pivoting actuation handle mounted for movement relative to the stationary handle. Jaw operating means are operatively connected between the pivoting actuation handle and the cooperating jaws of the end effector for effectuating cooperative movement of the jaw members. In addition, articulation means are operatively connected between the handle assembly and the articulation coupler for effectuating articulated angular movement of the articulation coupler relative to the longitudinal axis of the outer instrument shaft.

In one embodiment of the subject invention, the jaw operating means includes a relatively short distal actuation ram extending through the yoke assembly and a relatively longer proximal actuation ram extending from the handle assembly through the outer shaft. A distal end of the distal actuation ram is operatively connected to the cooperating jaw members of the end effector by way of a transverse cam pin, and a proximal end of the distal ram is operatively connected to the distal end of the longer proximal actuation ram.

In another embodiment, the jaw operating means includes a torque cable having a distal end operatively connected to a cam pin that is operatively associated with the cooperating jaws of the end effector and a proximal end that is operatively connected to a cable coupler connected to the pivoting actuation handle.

In one embodiment of the invention, the articulation means includes two actuation shafts, including a static inner actuation shaft and a dynamic inner actuation shaft. The static actuation shaft extends distally from the outer instrument shaft and is pivotably connected to the articulation coupler by a first pivot pin that is stationary. The dynamic inner actuation shaft extends distally from the outer instrument shaft and is pivotably connected to the articulation coupler by a second pin that moves in an angled slot for effectuating articulated angular movement of the articulation coupler relative to the longitudinal axis of the outer instrument shaft. In another embodiment, the articulation means includes an articulation cable extending through the outer instrument shaft between an articulation coupler control knob operatively associated with the handle assembly and the articulation coupler at the distal end of the shaped outer instrument shaft.

In an embodiment of the subject invention, the yoke assembly or rotation coupler is mounted for axial rotation relative to the articulation coupler. In this case, the handle assembly includes an end effector rotation knob operatively connected to yoke assembly for effectuating the axial rotation thereof relative to the articulation coupler. In addition, the handle assembly includes an outer shaft rotation knob operatively connected to the outer instrument shaft for rotating the outer instrument shaft about the longitudinal axis thereof together with the actuation member or ram shaft.

These and other features of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use novel laparoscopic hand instruments the subject invention without undue experimentation, preferred embodiments thereof will be described in detail herein below with reference to certain figures, wherein:

FIG. 1 is a side elevational view of a laparoscopic hand instrument constructed in accordance with a preferred embodiment of the subject invention;

FIG. 2 is an enlarged cross-sectional view of the barrel portion of the handle assembly of the laparoscopic hand instrument shown in FIG. 1, illustrating the components located herein;

FIG. 6 is an exploded perspective view of the proximal end portion of the actuation ram with the coupler insert that connects the actuation ram to the pivoting actuation handle;

FIGS. 7 through 10 are cross-sectional views of shaped instrument shafts of different geometries that are configured to resist bending and support the actuation ram;

FIGS. 20 and 21 are perspective views of the distal portions of two instrument shaft assemblies constructed in accordance with the subject invention wherein the shaft has a beam-shaped configuration for added strength and rigidity;

DETAILED DESCRIPTION OF PREFERRED EMBODIMENTS

Figure 3:
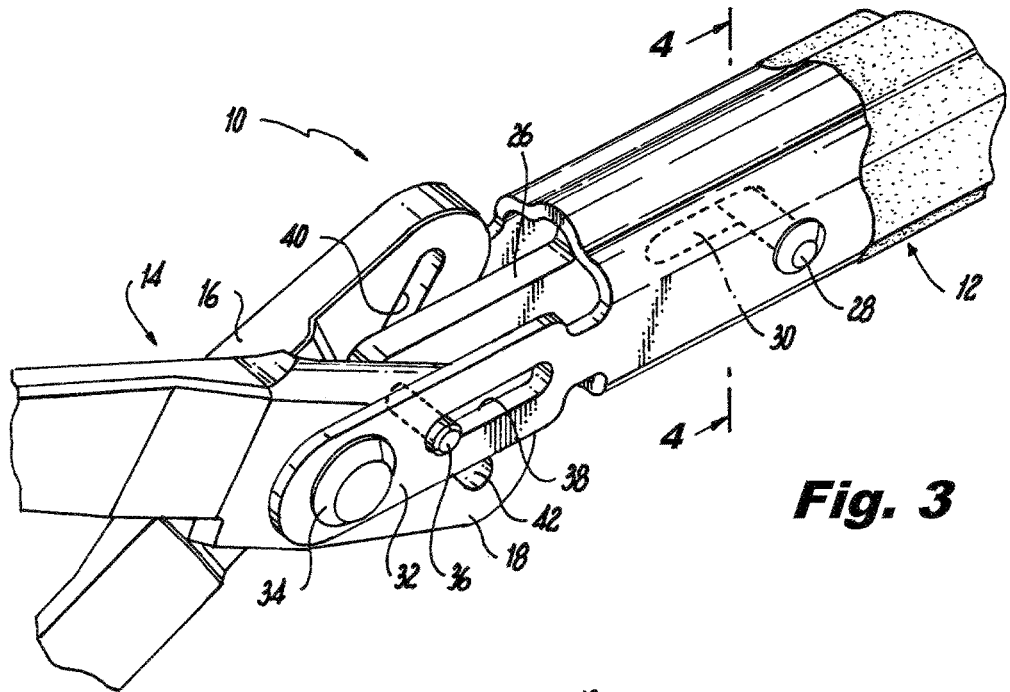
FIG. 3 is an enlarged perspective view of the end effector of the hand instrument shown in FIG. 1, with the cooperating jaws shown in an open position.

Referring now to the drawings, wherein like reference numerals identify similar structural features or aspects of the subject invention, there is illustrated in FIG. 1 a surgical instrument constructed in accordance with a preferred embodiment of the subject invention and designated generally by reference numeral 10.

Referring now to FIG. 1, surgical instrument 10 is intended for use in laparoscopic surgical procedures performed through a pneumatically sealed surgical access device, such as that which is disclosed, for example, in commonly assigned U.S. Pat. No. 8,795,223, the disclosure of which is herein incorporated by reference in its entirety. This device uses a pressurized gas to effectively seal the interface between the outer shaft of the surgical instrument and the inner wall of the tubular trocar sheath through which it passes instead of conventional mechanical seals, gaskets or lubricants.

As best seen in FIG. 3, surgical instrument 10 includes an elongated shaped outer instrument shaft 12 having opposed proximal and distal end portions, and a non-circular cross-sectional profile. The instrument 10 is able to be constructed with a non-circular cross-sectional profile, rather than a conventional circular cross-sectional profile, because it is being used with a pneumatically sealed surgical access device, which does not require a tight mechanical seal between the outer periphery of the shaped instrument shaft 12 and the cylindrical inner periphery of the trocar sheath through which is passes to access the abdominal cavity of a patient during a surgical procedure.

Figure 11:
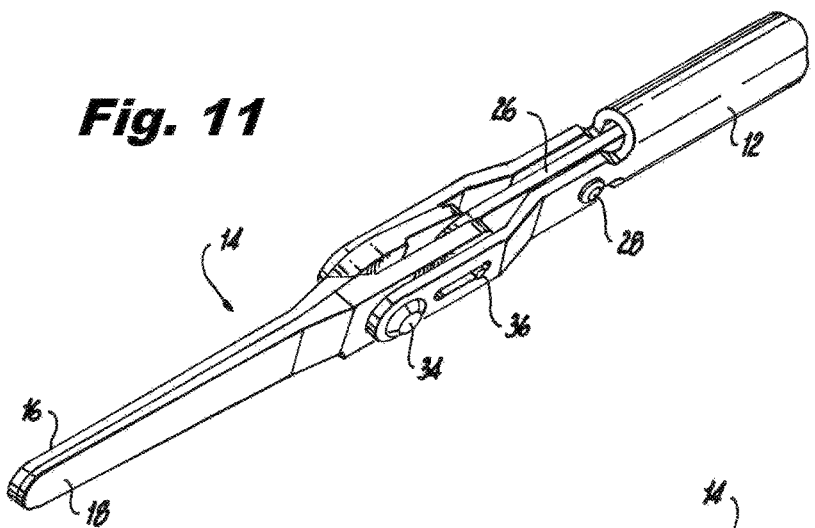
FIG. 11 is a perspective view of another end effector which is operatively associated with a relatively narrow shaped instrument shaft, with the cutting jaws of the end effector in a closed condition.

An end effector 14 is operatively associated with a distal end portion of the elongated shaped outer shaft 12. The end effector 14 includes a pair of cooperating jaw members 16 and 18 configured for movement between open and closed positions. The end effector 14 can be configured to perform a variety of different surgical tasks. For example, the cooperating jaw members 16 and 18 of end effector 14 can be configured as scissors for cutting tissue as shown in FIGS. 3 and 11, or the cooperating jaw members 16 and 18 of end effector 14 can be configured as graspers with interlocking rows of offset teeth, as shown for example in FIG. 12.

The surgical instrument 10 also includes a proximal handle assembly 20 having a barrel portion 22, a stationary gripping handle 23 and pivoting actuation handle 24, which may be provided with a ratcheted position locking mechanism (not shown). The handle assembly 20 is ergonomically constructed so that it can be held and operated with one hand.

Figure 4:
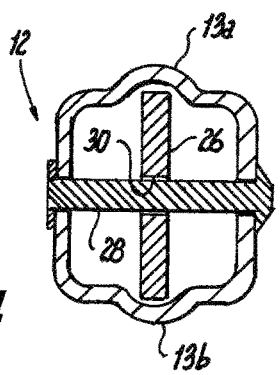
FIG. 4 is a cross-sectional view of the shaped outer instrument shaft and the elongated actuation ram taken through the guide pin along line 4-4 of FIG. 3.

Referring to FIGS. 2 and 3, an elongated ram or actuation member 26 extends through the elongated outer shaft 12 from the proximal handle assembly 20 to the end effector 14. As discussed in more detail below, movement of the pivoting actuation handle 24 will cause linear movement of the actuation member 26 in either a distal or a proximal direction, to cause corresponding movement of the cooperating jaw members 16 and 18 between open and closed portions. As best seen in FIGS. 3 and 4, the upper and lower surfaces of the relatively square outer shaped shaft 12 of instrument 10 have outwardly projecting ridges or bumps 13a, 13b that will keep the actuation member or ram 26 properly oriented during its proximal and distal travel.

As discussed further below, the actuation member 26 and outer instrument shaft 12 are adapted and configured to axially rotate together. In this regard, the outer shaft 12 includes a pair of proximally extending bent tabs 15 and 17 shown in FIG. 5, which reside in an annular channel 19 formed in the barrel portion 22 of the handle assembly 20, as seen in FIG. 2. This engagement restricts the linear movement of the outer shaft 12 relative to the handle assembly 20, while permitting axial rotation of the outer shaft 12 about its axis relative to the handle assembly 20.

The actuation shaft or ram 26 has a generally rectangular cross-sectional configuration and is well suited for use with a variety of different shaped instrument shafts. Examples of a variety of shaped instrument shafts are shown in FIGS. 7 through 10. In each instance, the shaped outer instrument shaft would be covered with heat shrink tubing that would fully conform to the shape of the shaft, as shown for example in FIG. 3.

A shaped outer instrument shaft 12a having a fully closed square cross-sectional profile is shown in FIG. 7. A shaped outer shaft 12b that has an open square cross-sectional profile is shown in FIG. 8. A shaped outer shaft 12c that has an open square cross-sectional profile with inwardly turned free ends is shown in FIG. 9, and a shaped outer shaft 12d that has an opened square cross-sectional profile and inwardly projecting side walls is shown in FIG. 10. The shaped outer shafts 12b-12d of FIGS. 8 through 10, respectively, are designed to isolate and hold the actuation ram 26 extending therethrough.

Those skilled in the art will readily appreciate that an instrument shaft having a square shape will have equal resistance to bending from side to side or corner to corner. It should also be appreciated that there are manufacturing advantages associated with having a shaped instrument shaft as described herein, in that the shaft can be stamped from a flat sheet of metal with all of the necessary slots and apertures for pins and rivets provided therein and then subsequently bent or otherwise formed into a final shape. It is also envisioned that the shaped instrument shaft of the subject invention could be extruded or injection molded with internal features such as lumens.

Figure 12:
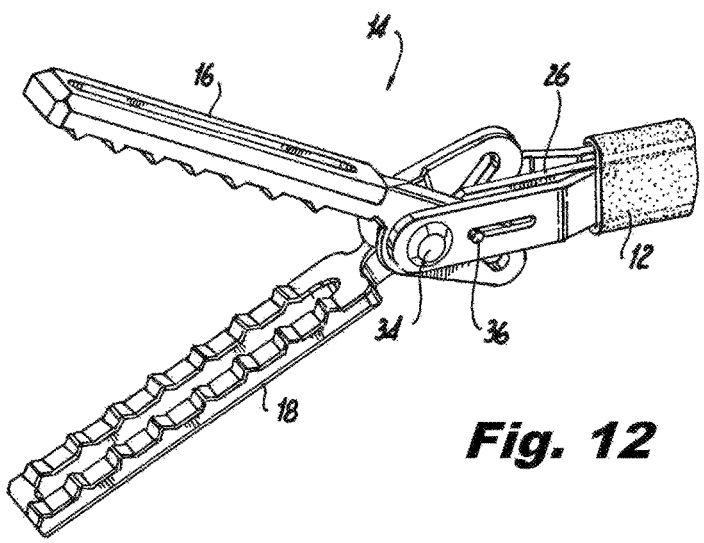
FIG. 12 is a perspective view of yet another end effector which is operatively associated with a relatively narrow shaped instrument shaft, with the grasping jaws in an open condition.

It is further envisioned that the outer instrument shaft 12 can be formed in a relatively narrow configuration so that the width-wise dimension of the shaped shaft is less than the height-wise dimension of the shaped shaft, as shown for example in FIGS. 11 and 12. In such instances, the actuation member or ram 26 will be more intimately enclosed within the shaped instrument shaft 12, providing greater structural stability to the actuation member 26 so as to inhibit bending.

Those skilled in the art will readily appreciate that a thin rectangular structure will inhibit bending more in the longer side of the rectangle than on the shorter side of the rectangle.

Referring now to FIG. 3, the distal end portion of the actuation member 26 is operatively connected to the outer instrument shaft 12 by a transverse guide pin 28 that resides within a linear guide slot 30 formed in the actuation member 26. This engagement is also shown in 4. The distal end portion of the outer shaft 12 includes a bifurcated yoke section 32 with two parallel yoke arms 32a, 32b for accommodating the cooperating jaw members 16 and 18 of the end effector 14. The cooperating jaws 16 and 18 are pivotably connected to the arms of the yoke 32 by a transverse yoke pin 34.

The distal end portion of the actuation member or ram 26 is also operatively connected to the cooperating jaw members 16 and 18 of the end effector by a transverse cam pin 36. The transverse cam pin 36 travels within linear cam slots 38 formed in each arm of the bifurcated yoke section 32 of the outer shaft 12 and within oppositely angled cam slots in 40 and 42 each of the jaw members 16 and 18, respectively. Preferably, the cam pin 36 is press fit into the distal end portion of the actuation member 26 and it has a clearance fit within the angled jaw member cam slots 40 and 42 and the linear cam slots 38 in the yoke section 32.

Figure 5:
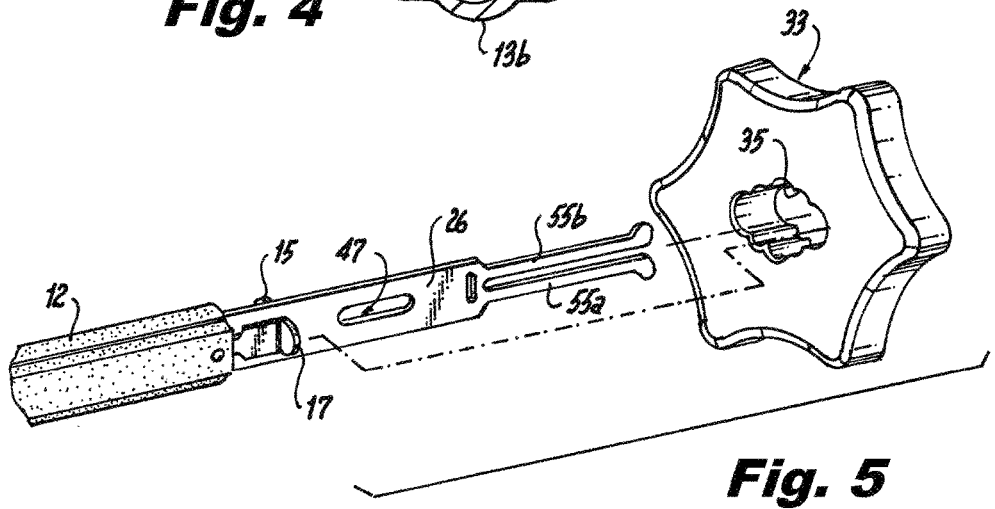
FIG. 5 is an exploded perspective view illustrating the connectivity of the proximal end portion of the shaped outer shaft and the shaft rotation knob.

As best seen in FIG. 5, the proximal end portion of the outer shaft 12 is operatively associated with a shaft rotation knob 33 that is supported in the barrel portion 22 of the proximal handle assembly 20 (see FIGS. 1 and 2). More particularly, the knob 33 is mounted to effectuate axial rotation of the outer instrument shaft 12 together with the actuation shaft 26 about the longitudinal axis thereof. The knob 33 includes a central lobed aperture 35 for cooperatively engagement with the outer shaft 12. To assemble this feature, the lobed aperture 35 in knob 33 is aligned with the proximal bent tabs 15 and 17 located on the proximal end of the outer shaft 12, and the knob 33 is then placed over the end of the outer shaft 12. Thereafter, the knob 33 is rotated 90 degrees to lock the outer shaft 12 into the lobed aperture 35.

Referring to FIG. 6, in one embodiment of the subject invention, a proximal end portion of the actuation member 26 includes a two-part symmetrical coupling 44a, 44b for operatively connecting the actuation member 26 to the pivoting actuation handle 24. When the two couplers 44a, 44b are used together and facing one another, they will fit and hold together through a plurality of symmetrically placed holes and posts, as shown. An engagement tab 45 extends from the inner surface of each coupler 44a, 44b for engaging a linear slot 47 formed in the proximal portion of actuation shaft 26. The linear slot 47 is longer than the individual tabs 45 because both tabs are engaged with the slot 47. Moreover, as best seen in FIG. 2, the symmetric couplers 44a, 44b are accommodated within a cylindrical chamber 49 formed in the barrel portion of the handle assembly 20. The two couplers 44a, 44b will move axially and rotationally within the chamber 49 in the barrel portion 22 of handle assembly 20, as best seen in FIG. 2.

With continuing reference to FIG. 6 in conjunction with FIG. 2, the actuation handle 24 has a keyhole feature 57, which includes a larger diameter portion configured for assembly over the larger diameter of the coupler 44a, 44b. Once over the larger diameter portion of the coupler, the smaller diameter area of the keyhole feature 57 will mate with the smaller outside diameter portion of the coupler, as shown in FIG. 2. When the actuation handle 24 is pivoted, it will move the couplers 44a, 44b which will move the actuation shaft 26 to actuate the jaws of the end effector 14.

Figure 13:
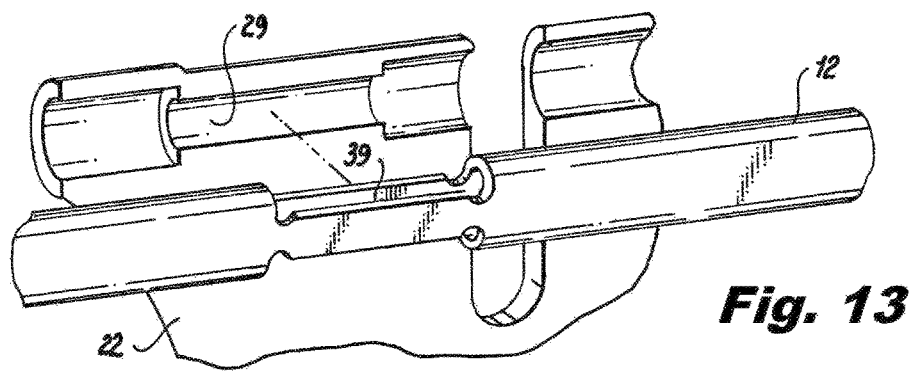
FIG. 13 is a perspective view of the proximal end portion of an outer shaft separated from the barrel portion of the handle assembly, wherein the proximal end portion of the outer shaft includes a stamped area configured to engage a complementary chamber in the barrel portion of the handle assembly to facilitate shaft rotation while inhibiting axial shaft movement.

Referring to FIG. 13, there is illustrated another manner of constraining the outer instrument shaft 12 within the barrel portion 22 of the proximal handle assembly 20. More particularly, an elongated notch is 39 is stamped and formed into the proximal end portion of the outer shaft 12 which is arranged within a cavity 29 formed in the barrel portion 22 so that it will not move linearly relative to the handle assembly 20 but it can still rotate axially with respect to the barrel portion of the handle assembly 20.

In one embodiment of the subject invention, the cooperating jaw members 16 and 18 are located inside of the arms of the bifurcated arms 32a, 32b or yoke section of instrument shaft 12, as shown for example in FIG. 20. In another embodiment of the subject invention, the cooperating jaw members 16 and 18 are located outside of the bifurcated arms 32a, 32b of the yoke section of the instrument shaft 12. It is envisioned that a biasing washer could be placed on the end effector pivot/yoke pin 34 between the cooperating jaw members 16 and 18 or between the arms of yoke section 32 and the jaw members 16 and 18 of the end effector 14 to more effectively tolerance the fit of the jaws members.

Referring once again to FIG. 2 in conjunction with FIG. 5, the proximal end portion of the actuation member 26 is cooperatively connected to a hollow banana plug-type electrical contact pin 50 for electro-cautery tasks. The banana plug or contact pin 50 is supported within the barrel portion 22 of the handle assembly 20 and is positioned over a pair of elongated flexible tabs 55a, 55b that project from the proximal end of actuation shaft 26. When the flexible tabs 55a, 55b are positioned with the interior bore 52 of the plug 50, the actuation shaft 26 is able to move linearly and rotationally without disengaging from the plug 50 so as to maintain constant electro-cautery connectivity.

Figure 14:
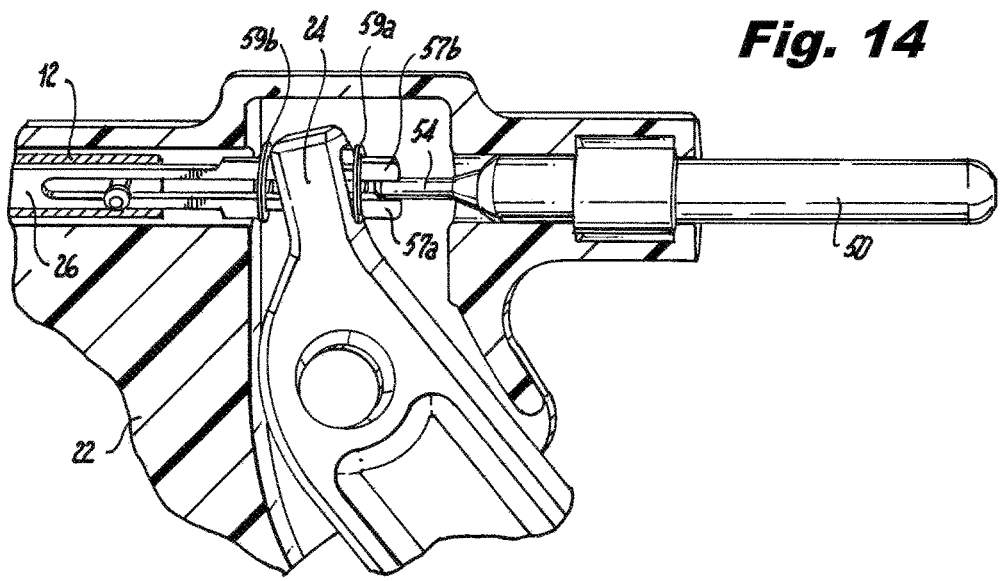
FIG. 14 is a side elevational view of the handle assembly, in cross-section, illustrating another type of connection between the pivoting actuation handle and the actuation ram, and wherein the actuation ram is connected to a banana plug for electro cautery tasks.

Referring now to FIG. 14, there is illustrated another way to connect the proximal end portion of actuation member or ram 26 to the pivoting actuation handle 24. In this case, flexible finger tabs 57a, 57b are stamped into the proximal portion of the actuation ram 26 which also has an undercut on the outer face thereof. The flexible tabs 57a, 57b are squeezed together to fit into a hole in the actuation handle 24 and then the undercut on the outer face of the actuation ram 26 outer face engages both sides of the actuation handle 24. When the handle 24 is pivoted or otherwise rotated, the actuation ram 26 will move linearly.

Proximal and distal washers 59a and 59b can be added to help increase the surface area of contact between the actuation handle 24 and the actuation ram 26 for a more robust fit. Also shown in FIG. 14 is another way to facilitate cooperative engagement between the actuation ram 26 and the banana plug 50. In this case, a small diameter post 54 on the plug 50 extends between the flexible tabs 57a, 57b of the actuation ram 26. This arrangement allows constant electrical contact between the two components, while the actuation ram 26 moves both linearly and rotationally.

Figure 15:
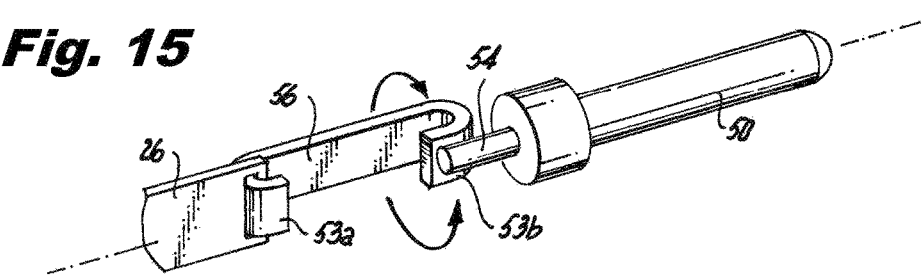
FIG. 15 is a perspective view of a coupling spring connected between the proximal end of the actuation ram and the distal tip of the banana plug associated with the handle assembly.
Figure 16:
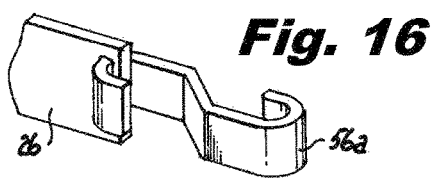
FIGS. 16 through 19 illustrate various embodiments of coupling springs connected to actuation rams, as shown in FIG. 15.
Figure 17:
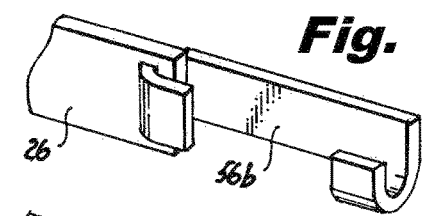
Figure 18:
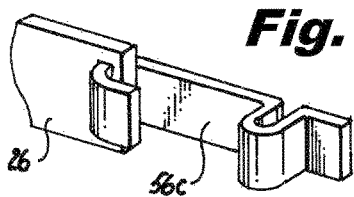
Figure 19:
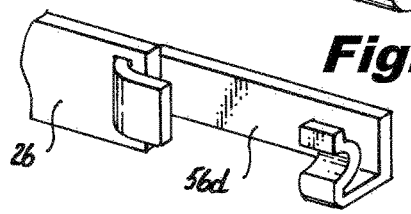
Figure 22:
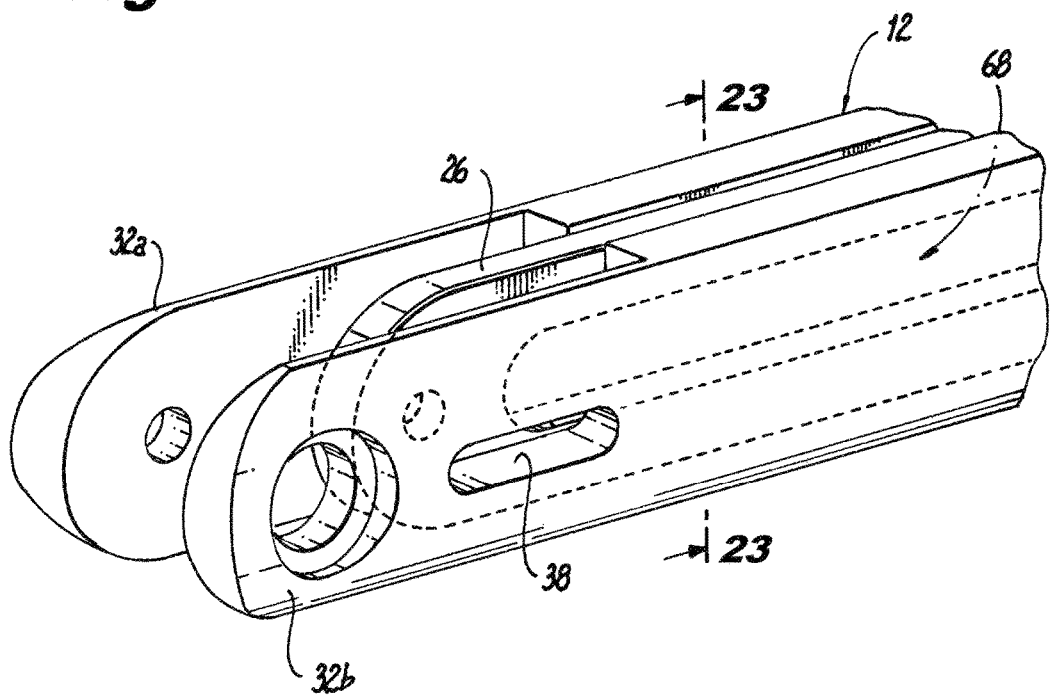
FIG. 22 is a perspective view of the distal portion of yet another shaped shaft assembly constructed in accordance with the subject invention, wherein the actuation ram is supported on an interior web of the beam shaped shaft.

Referring to FIG. 15, there is shown an alternative way of mechanically and electrically connecting the proximal end portion of the actuation ram 26 to a banana plug 50, using a leaf spring 56. More particularly, the hooked distal end 53a of the leaf spring 56 is mechanically connected to the proximal end of the actuation member 26, while the hooked proximal end 53b of the leaf spring 56 is in biased contact with the distal post 54 of the contact pin 50. Again, the electrical contact pin 50 is adapted and configured to be connected to a source of electrical energy, so that the end effector can be used to cauterize tissue during a surgical procedure. FIGS. 16 through 19 illustrate several different embodiments of leaf springs for mechanically and electrically connecting the proximal end portion of the actuation member 26 to the electrical contact pin 50. These include leaf springs 56a-56d, as shown.

Figure 23:
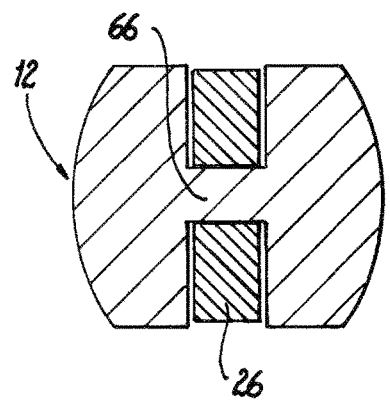
FIG. 23 is a cross-sectional view taken along line 23-23 of FIG. 22.

Referring now to FIGS. 20-25, in certain embodiments of the subject invention, the shaped outer shaft 12 of the instrument has a beam shaped configuration that includes a transverse central web section 66. One example is shown for example in FIGS. 22 and 23. In such an instance, the actuation member 26 includes a longitudinal slot 68 for accommodating the transverse web section 66 of the outer shaft 12, as shown in FIG. 23.

In an embodiment of the subject invention, the outer shaft 12 of the instrument 10 has a beam-type geometric configuration that includes opposed concave lateral supports 70a and 70b. In one instance, the opposed concave lateral supports 70a and 70b have a generally rectangular configuration, as shown in FIG. 21. In another instance, the opposed concave lateral supports 70a and 70b have a generally rounded configuration, as shown in FIG. 20. These beam-shaped outer shaft designs, which curve or bend away from the actuation ram 26, have a high resistance to bending in any direction. As further illustrated in FIG. 21, the pivot/yoke pin 34 associated with the cooperating jaws member 16 and 18 of the end effector 14 can take the form of a shoulder type rivet or the pin 34 could be constructed as a double rivet or two rivets inserted into a hollow central tube.

Figure 24:
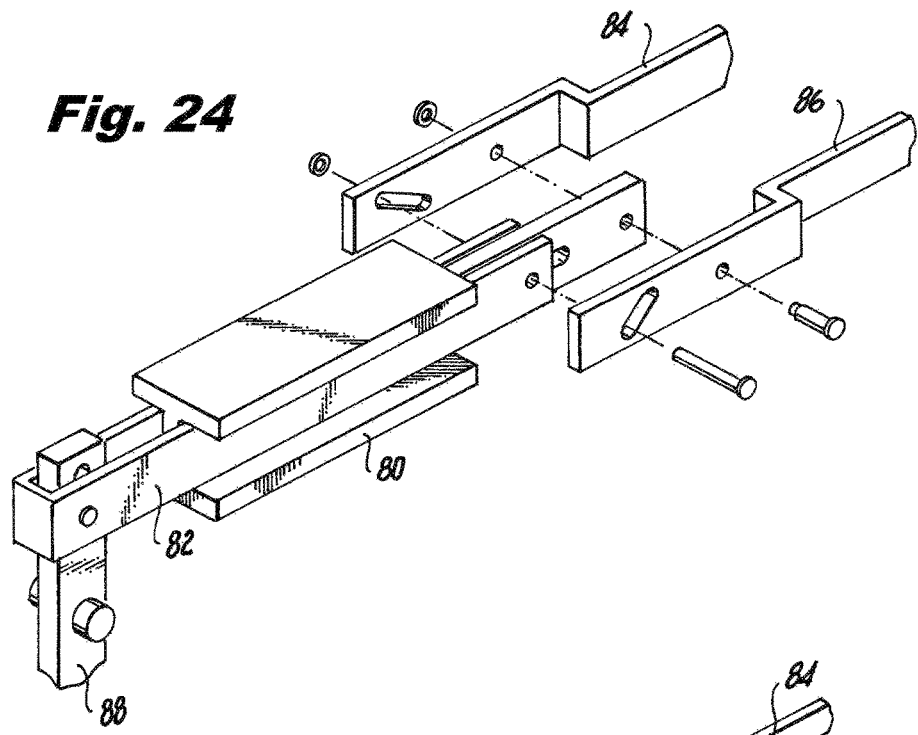
FIGS. 24 and 25 are exploded perspective views of the distal end portions of two other shaped shaft assemblies constructed in accordance with the subject invention, which include I-beam shaped instrument shafts.
Figure 25:
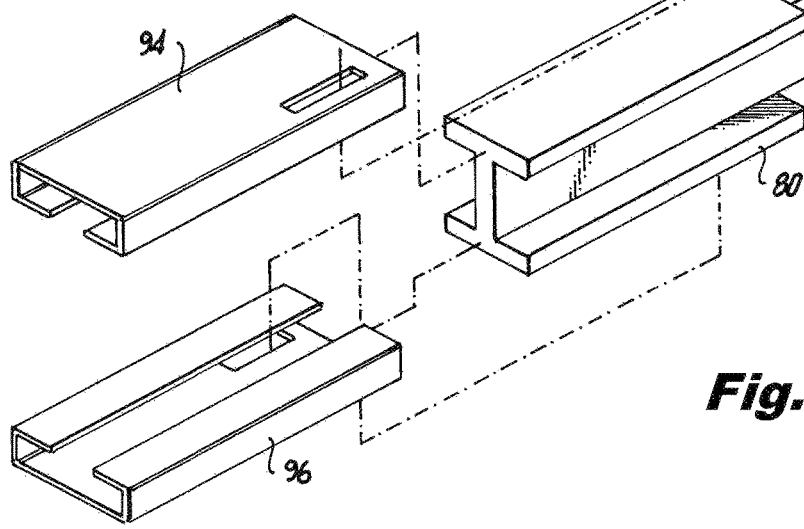

Referring now to FIGS. 24 and 25, there is illustrated two additional mechanical constructs of a beam shaped shaft 80 configured in accordance with the subject invention. The mechanical construct of FIG. 24 includes an elongated U-shaped actuation member 82 for controlling the movement of distal end effector s 84 and 86 using an actuation handle 88. The elongated "U" shaped actuation member 82 surrounds the central web of the beam shaped instrument shaft 80. The mechanical construct of FIG. 25 includes upper and lower rectangular actuation sleeves 94 and 96 that interlock with the upper and lower supports of the beam shaped instrument shaft 80. The upper and lower actuation sleeves 94 and 96 control the respective movement of corresponding distal end effectors 84 and 86.

Referring now to FIGS. 26 through 30, there is illustrated another surgical instrument 100 having a non-circular, substantially square outer instrument shaft which is configured with an articulating and rotating distal end portion for enhancing the operational range of movement of the device during laparoscopic surgical procedures.

Figure 26:
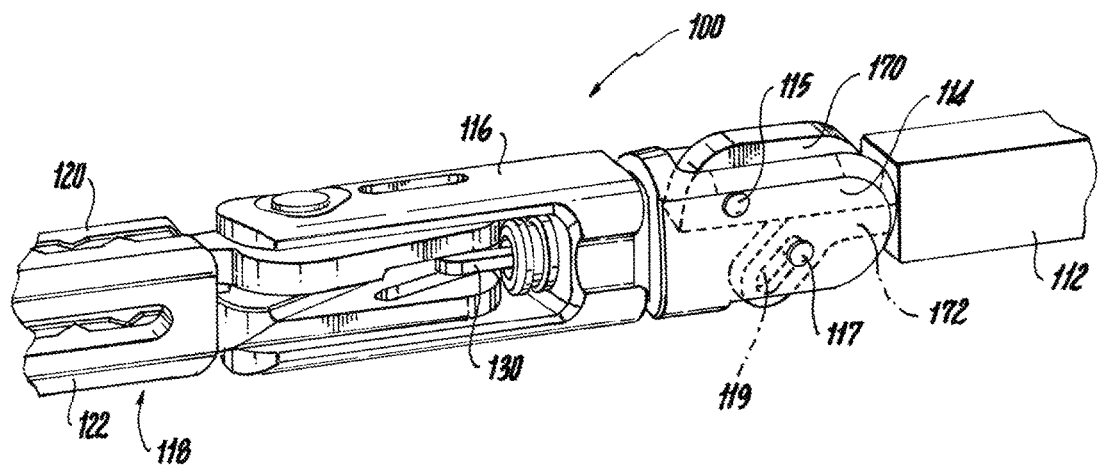
FIG. 26 is a perspective view of the distal end portion of a surgical hand instrument having a shaped instrument shaft assembly that is adapted and configured to articulate.
Figure 27:
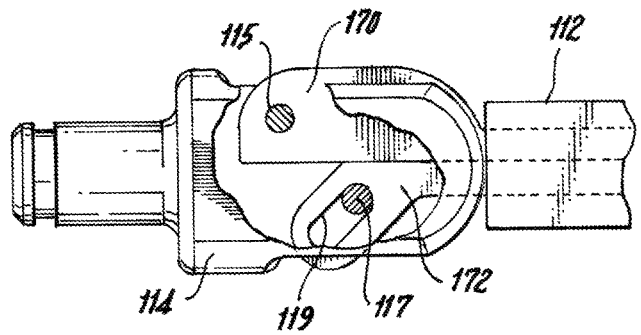
FIGS. 27 and 28 are side elevational views, with the wall of the articulation coupler broken away, to illustrate the static and dynamic actuation members of the articulation mechanism for the instrument shaft assembly shown in FIG. 26.
Figure 28:
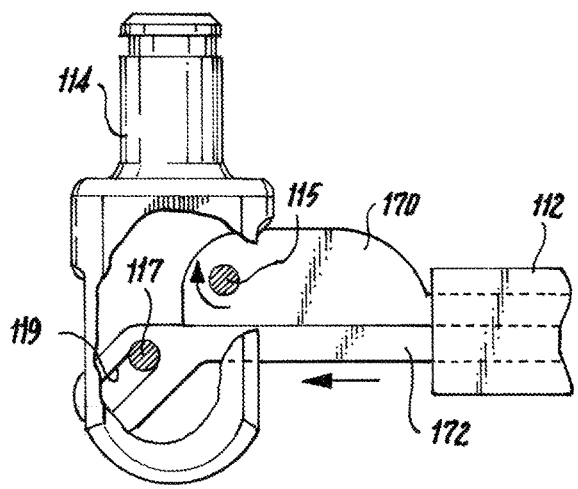

Referring to FIGS. 26-28, there is illustrated an articulating surgical instrument 100 constructed in accordance with a preferred embodiment of the subject that includes an elongated outer shaped instrument shaft 112 having opposed proximal and distal end portions, and a non-circular cross-sectional profile. The surgical instrument 100 includes an articulation coupler 114 operatively associated with a distal end portion of the outer instrument shaft 112. The articulation coupler 114 has a central axis and is mounted for articulated angular movement relative to a longitudinal axis of the elongated outer shaft 112. More particularly, the articulating coupler 114 is mounted to pivot 90 degrees relative to the longitudinal axis of the outer instrument shaft 112.

A yoke assembly 116 is operatively associated with the articulation coupler 114, and an end effector 118 is operatively associated with the yoke assembly 116. The end effector 118 includes a pair of cooperating jaw members 120 and 122 configured for movement between open and closed positions.

In an embodiment of the subject invention shown in FIGS. 26-28, the articulation means includes a static inner actuation shaft 170 extending distally from the outer instrument shaft 112 and pivotably connected to the articulation coupler 114 by a pin 115, and a dynamic inner actuation shaft 172 extending distally from the outer instrument shaft 112 and pivotably connected to the articulation coupler 114 by a pin 117 through an angled slot 119 for effectuating articulated angular movement of the articulation coupler 114 relative to the longitudinal axis of the outer instrument shaft 112.

Figure 36:
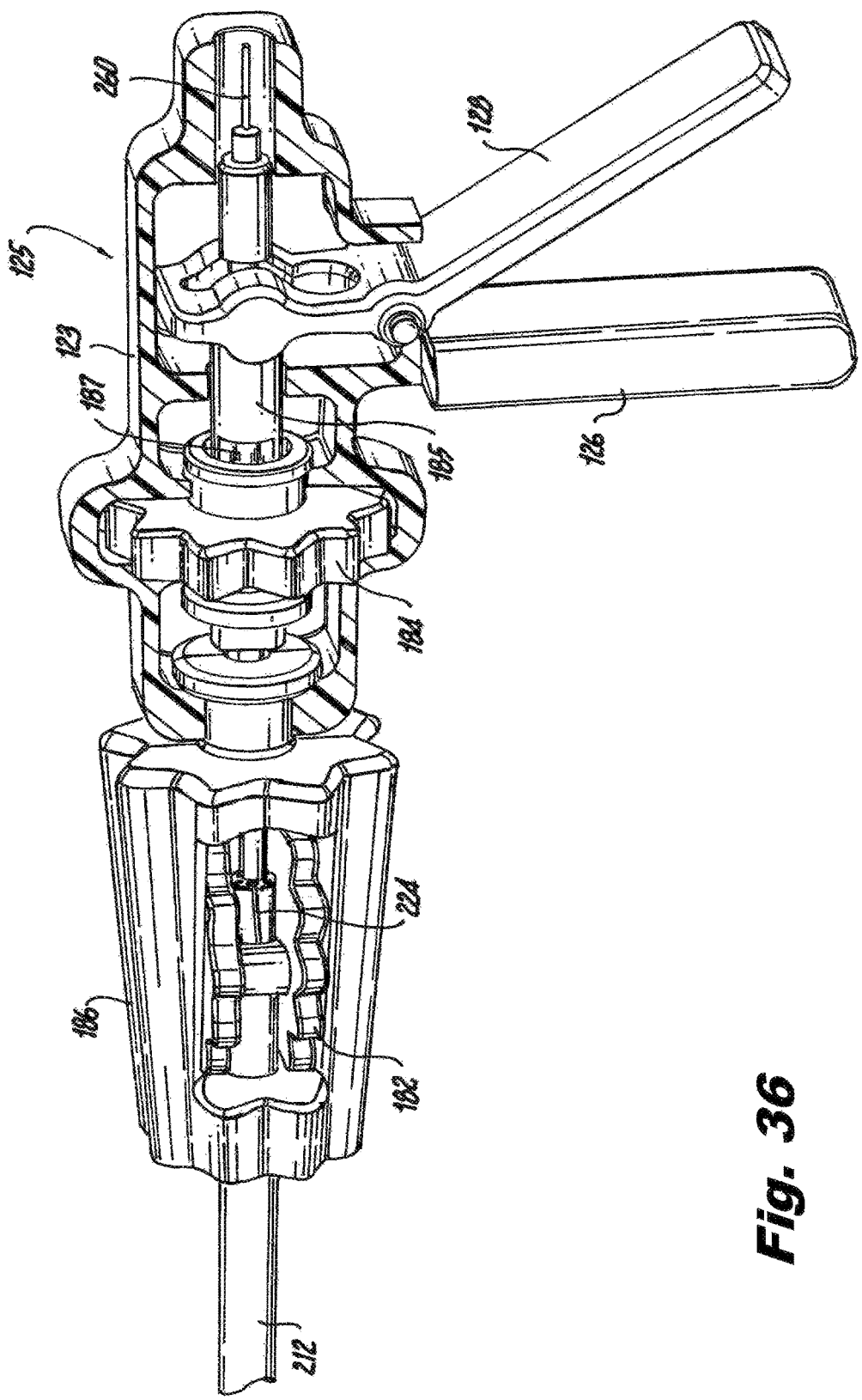
FIG. 36 is a perspective view of the handle assembly associated with the articulated shaft assembly of FIGS. 34 and 35, with the barrel portion in cross-section to illustrate the components housed therein.
Figure 37:
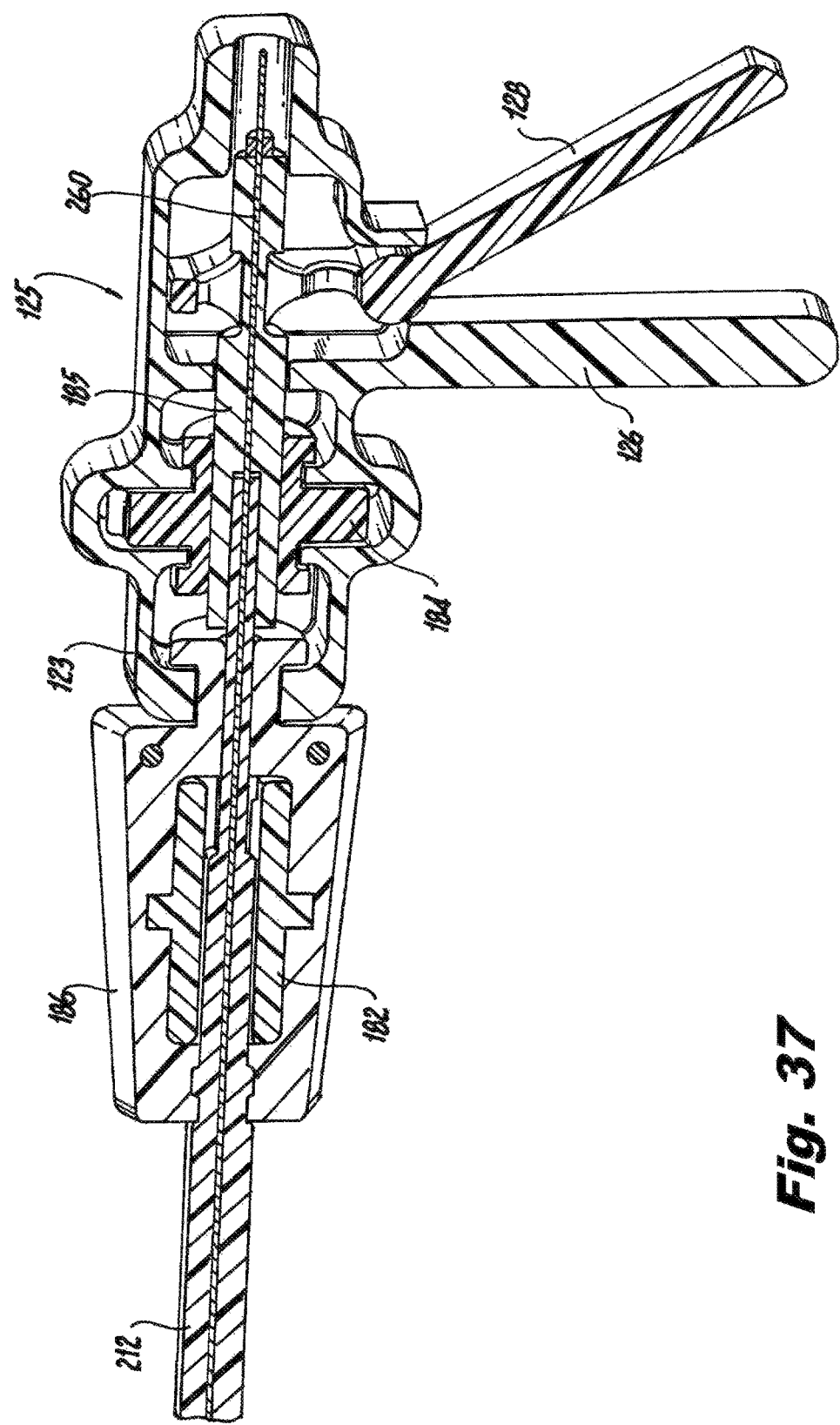
FIG. 37 is a more detailed cross-sectional view the handle assembly associated with the articulated shaft assembly of FIGS. 34 and 35.

Referring to FIGS. 36 and 37, the surgical instrument 100 further includes a proximal handle assembly 125 having a barrel portion 123, stationary handle 126 and a pivoting actuation handle 128. Jaw operating means, which are described in greater detail below, are operatively connected between the pivoting actuation handle 128 and the cooperating jaws members 120 and 122 of the end effector 118 for effectuating cooperative movement of the jaw members 120 and 122. In addition, articulation means, which are also described in more detail below, are operatively connected between the handle assembly 125 and the articulation coupler 114 for effectuating articulated angular movement of the articulation coupler 114 or yoke assembly 116 relative to the longitudinal axis of the outer instrument shaft 112.

Figure 33:
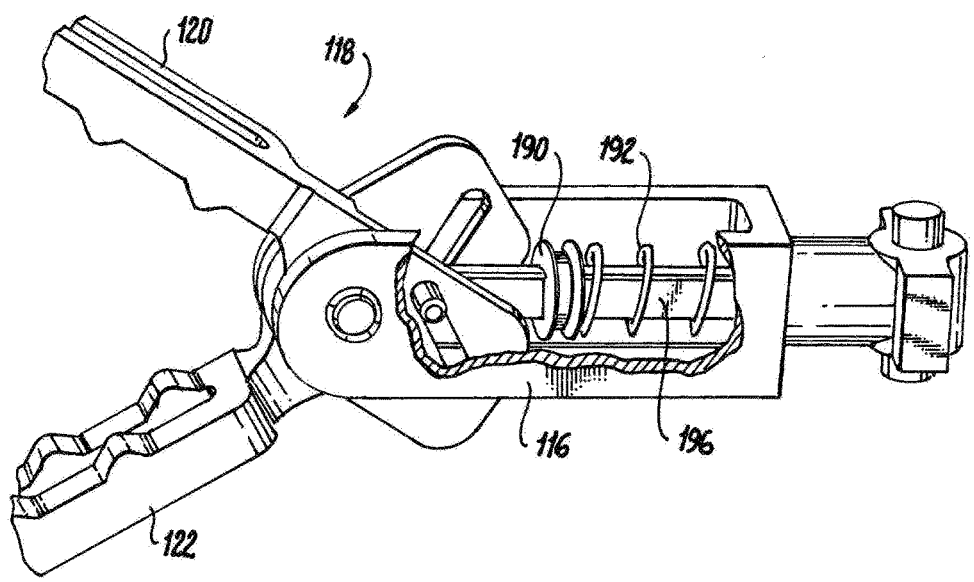

In one embodiment of the subject invention shown in FIGS. 26 and 33, the jaw operating means includes a relatively short distal actuation ram 130 extending through the yoke assembly 116. A distal end of the distal actuation ram 130 is operatively connected to the cooperating jaw members 120 and 122 of the end effector 118 by a cam pin. The proximal end of the distal actuation ram 130 is operatively connected to a longer actuation ram 132 that extends through the outer shaft from the handle assembly. That is the jaw operating means also includes a relatively long proximal actuation ram 132 extending through the elongated outer instrument shaft 112 from the proximal handle assembly 125 to the yoke assembly 116.

A proximal end of the proximal actuation ram 132 is operatively connected to the pivoting actuation handle 128. The short actuation ram 130 could also be connected to a torque cable, or to a nut that runs along a lead screw. Furthermore, it is envisioned that the shorter distal ram could connect to the proximal longer ram or to a torque cable. This connection could be made with a ball joint (not shown) or a universal joint (also not shown).

Figure 29:
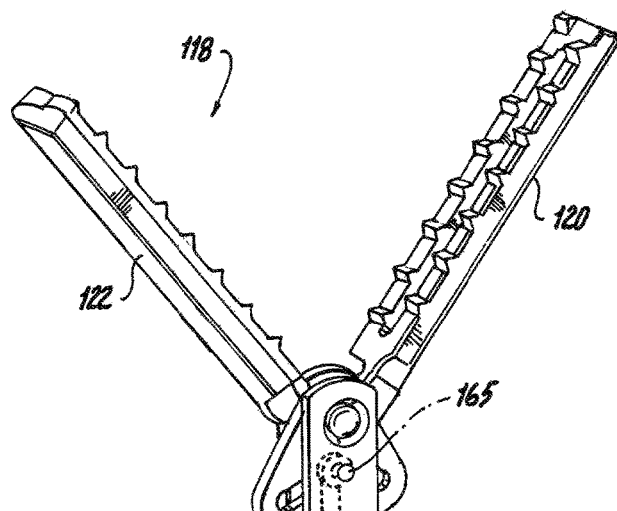
FIGS. 29 and 30 are perspective views of an embodiment of the articulating hand instrument of the subject invention that includes an actuation cable for controlling the movement of the jaws of the end effector.
Figure 30:
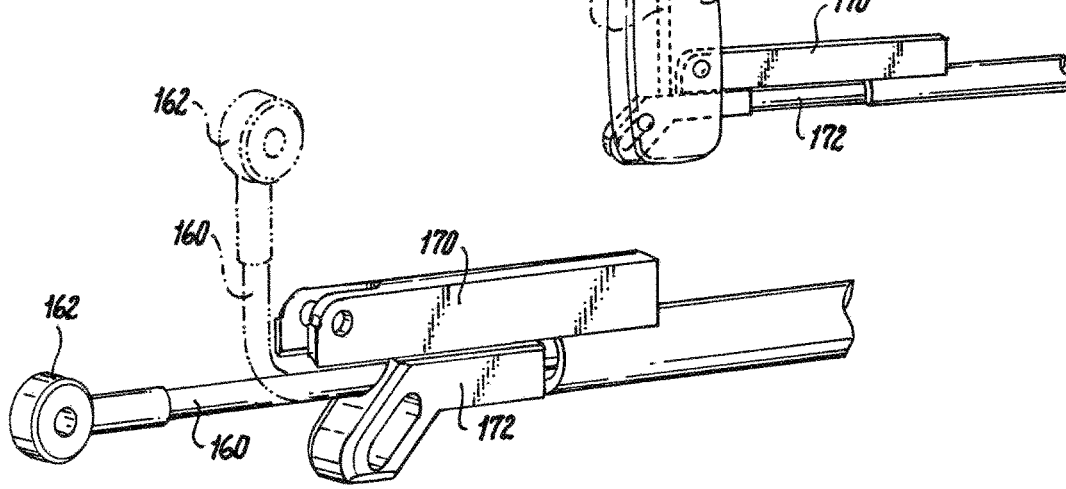

In another embodiment shown in FIGS. 29 and 30, the jaw operating means includes a flexible torque cable 160 for controlling the end effector 118. The torques cable 160 has a distal end grommet 162 operatively connected to a cam pin 165 that is operatively associated with the cooperating jaws 120 and 122 of the end effector 118. A proximal end of the torque cable 160 is operatively connected to a cable coupler 185 connected to the pivoting actuation handle 128, as best seen in FIG. 37. The torque cable 160 allows the articulation coupler 114 to move 90 degrees and still transmit both a rotational element to the end effector 118 and a linear movement to open and close the jaws 120 and 122 of the end effector 118.

Figure 31:
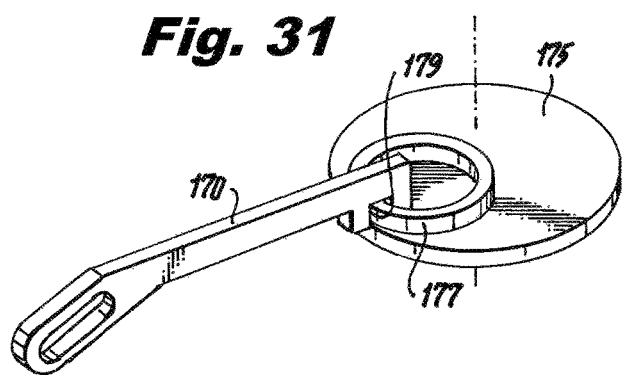
FIG. 31 is a perspective view of a mechanism for controlling the movement of the dynamic actuation member shown in FIGS. 27 and 28.

Referring to FIG. 31, there is shown a way to move the dynamic inner actuation shaft 170 shown in FIGS. 26 through 30. That is, double non-coaxial discs 175, 177 form a knob at the proximal end of the instrument. The smaller non-coaxial disc 175 engages notches 179 in the proximal end of the dynamic inner actuation shaft 170. As the user rotates the disc 175, 177, the dynamic inner actuation shaft 170 will move linearly and distally, thereby articulating the distal end portion of the instrument.

FIG. 33 shows an alternate way to open and close the jaw members 120 and 122 of end effector 118. In this case a retainer ring 190 and spring 192 within the rotating yoke assembly or coupler 116 biases the actuation ram 196 to a fully distal position, keeping the end effector jaws 120 and 122 in an open state. As the user squeezes the actuation handle 128, the actuation ram 196 or a torque cable will move distally and close the end effector 118. Releasing tension on the handle 128 will let the distal spring 192 automatically open up the end effector 118.

Figure 34:
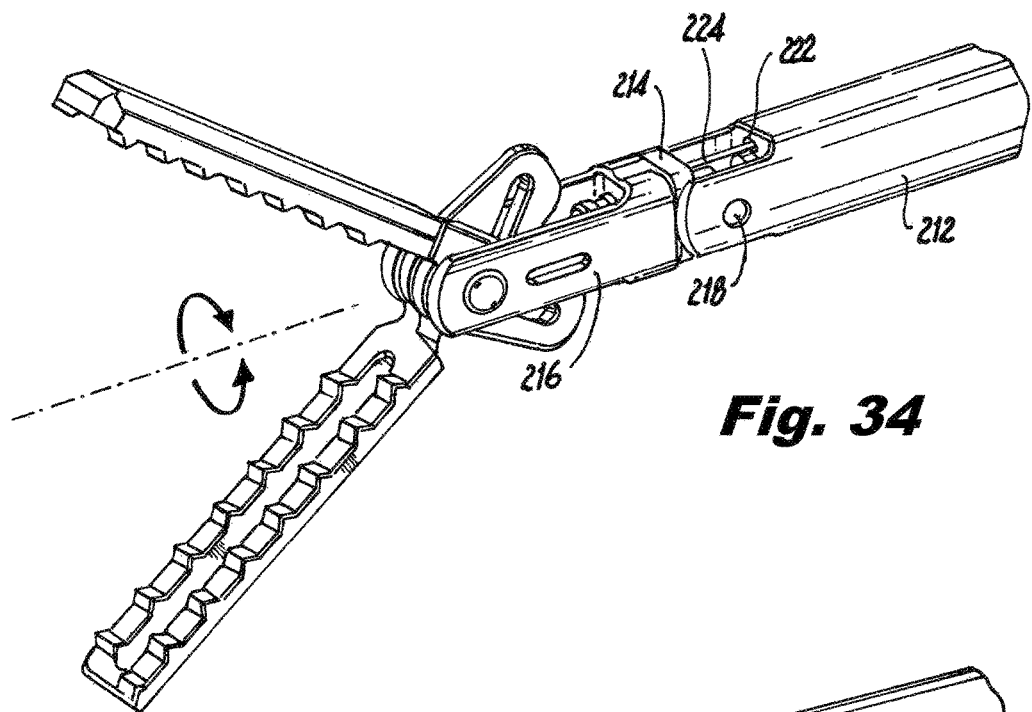
FIGS. 34 and 35 illustrate an articulated shaped shaft assembly constructed in accordance with the subject invention, which includes a rotation coupled yoke assembly configured for axial rotation relative to the articulation coupling of the shaft assembly.
Figure 35:
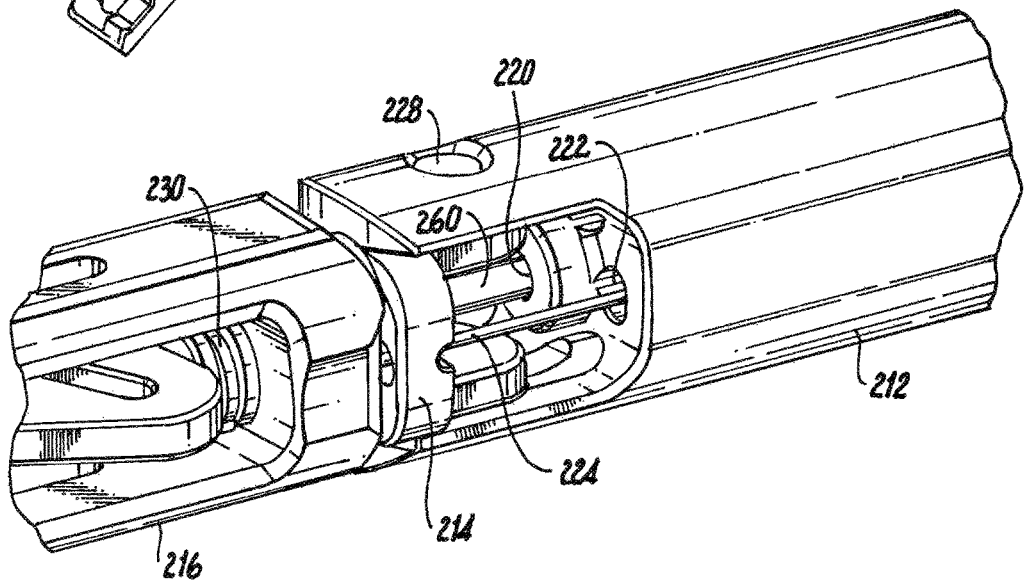

Referring to FIGS. 34 through 36, there is shown an embodiment of the subject invention wherein the articulation means includes a looped articulation coupler cable extending through the outer instrument shaft 212, between an articulation coupler control knob 182 associated with the handle assembly 125 and the articulation coupler 214.

Figure 32:
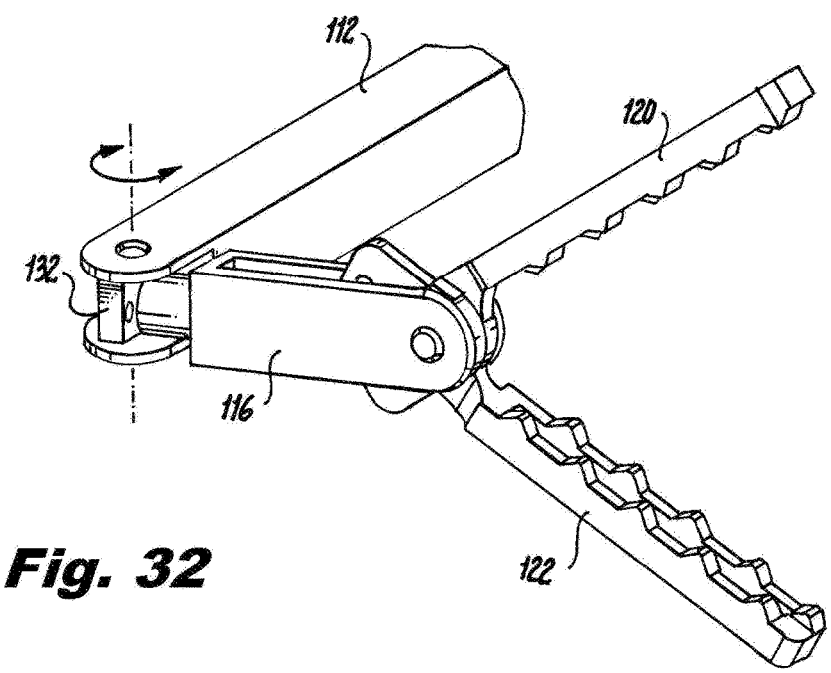
FIGS. 32 and 33 illustrate an articulating end effector constructed in accordance with the subject invention.

In this embodiment, the outer instrument shaft 212 is either an extrusion or an injection molded structure and it has multiple full length inner lumens formed therein. The center lumen 220 is dimensioned for either a torque cable 260 or a long actuation ram, as shown for example in FIG. 32. The outer lumens 222 on either side of the center lumen 220 accommodate cables 224 to activate the articulation coupler 214. The pivot point 228 is provided for the articulation coupler 214. The articulation coupler 214 extends into the rotation coupler 216 and is held in place with the use of retaining rings 230 or C-shaped clips.

Referring to FIGS. 36 and 37, the yoke assembly or rotational coupler 216 is mounted for rotation relative to the articulation coupler 214, as depicted in FIG. 34. In this case, the handle assembly 125 includes an end effector rotation knob 184 operatively connected to rotational coupler 216 for effectuating the axial rotation thereof relative to the articulation coupler 214. The actuation handle 128 will open and close the end effectors 118. This is done via a torque cable coupler 185, wherein the torque cable 260 is inserted inside the coupler and crimped proximally. The actuation handle fits over the torque cable 185 coupler similar to the symmetrical coupler previously already disclosed.

The torque cable coupler 185 also has flats 187 on its outside to mate with the end effector knob 184. By rotating the end effector knob 184 the torque cable coupler 185 rotates, which will rotate the torque cable 260. A feature can be added to the crimp area to help rotation (not shown).

In addition, as best seen in FIGS. 36 and 37, the handle assembly 125 includes an outer shaft knob 186 operatively connected to the outer instrument shaft 212 for rotating the outer instrument shaft 212 about the longitudinal axis thereof. The handle assembly 125 also includes an articulation knob 182 that holds the proximal ends of the articulation cables 224 which extend from the articulation coupler 214 and pivot within the shaft rotation knob 186. As the articulation knob 182 is rotated, the cables 224 get pulled proximally and activate the articulation coupler 214. The shaft rotation knob 186 fits to the outer shaft 212 via grooves and flats. When it is rotated along with the articulation knob 182, the cables 224 do not twist.

Figure 38:
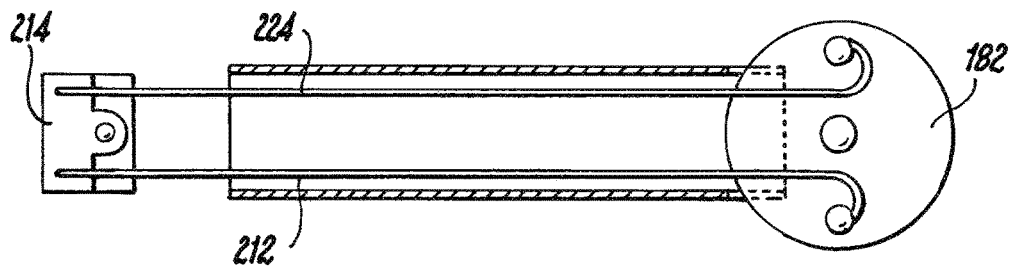
FIGS. 38 through 40 illustrate mechanisms for moving an articulation cable, as shown in FIG. 36.
Figure 39:
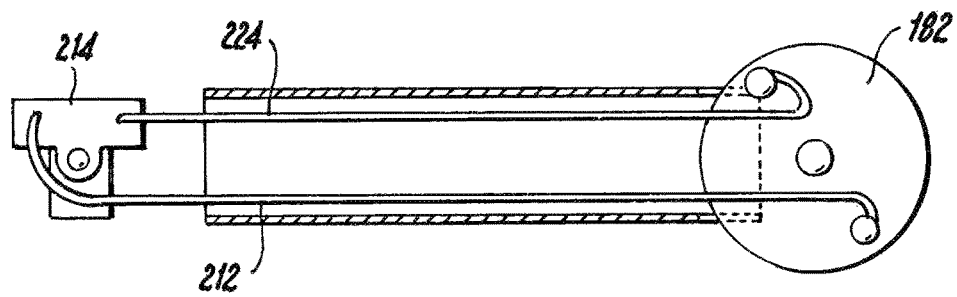

Referring to FIGS. 38 through 39, there is illustrated a mechanical construct depicting how the articulation coupler cable 224 is arranged to effectuate articulation of the articulation coupler 214. In this construct, the cable 224 is connected between the distal articulation coupler 214 and the proximal articulation coupler knob 182 such that one side of the looped cable 224 is pulled proximally under tension, and the opposite side of the looped cable 224 will slacken to allow articulation.

Figure 40:
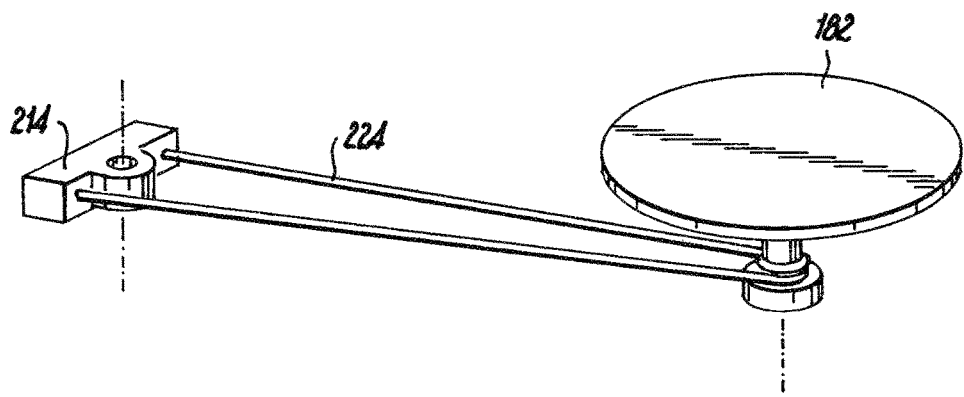

FIG. 40 shows another way to connect the proximal ends of the articulation cable 224 to the articulation coupler knob 182 in a configuration that resembles a boat rigging design, wherein the looped cable 224 is wrapped around a knob 182. By rotating the knob 182, the cable 224 will activate the articulation coupler 214.

Figure 41:
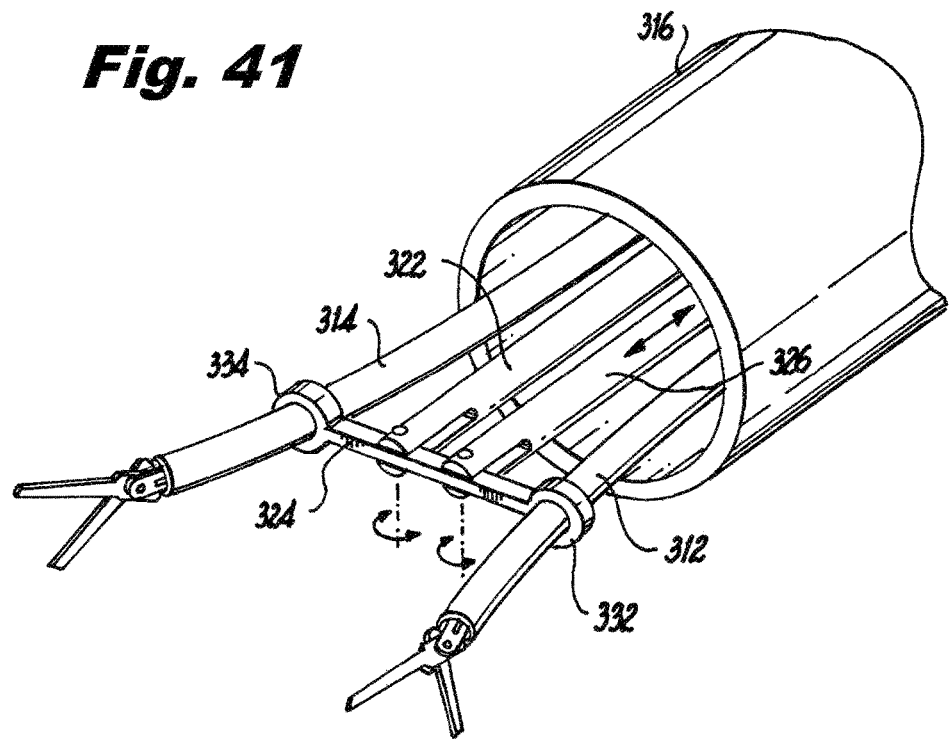
FIG. 41 illustrates a mechanism for moving two laparoscopic instrument shafts extending from the distal end of a cannula tube using a static control rod and a dynamic control connected by a pivotable link.
Figure 42:
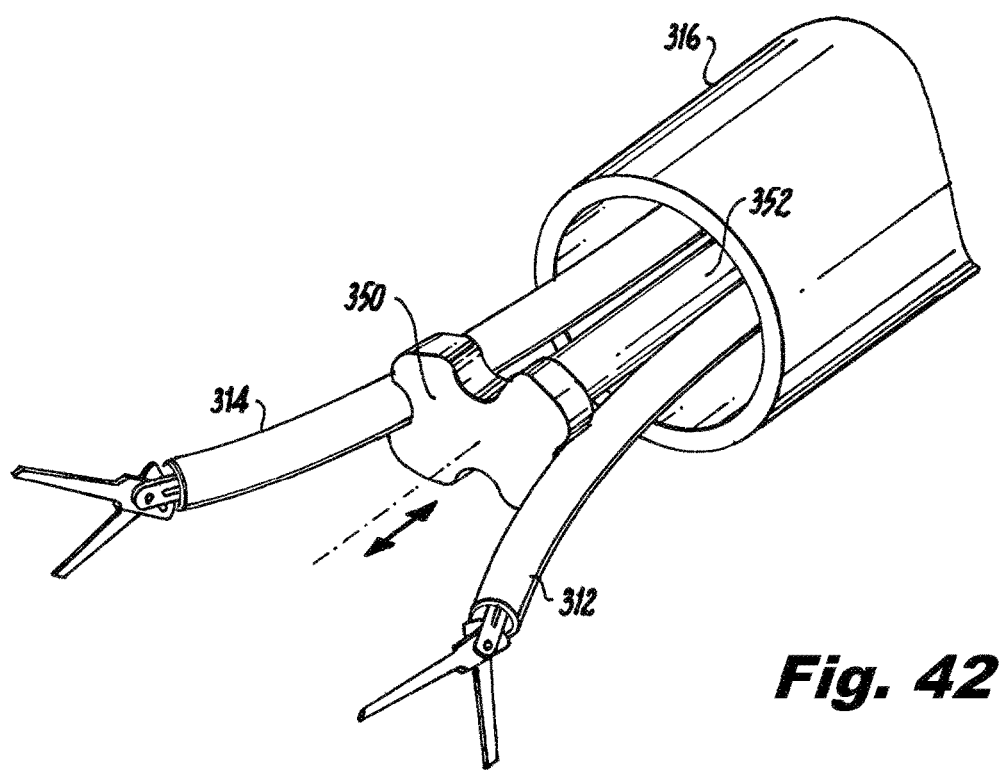
FIG. 42 illustrates a cammed separator mechanism for separating to laparoscopic instruments extending from the distal end of a cannula tube.

Referring now to FIGS. 41 and 42, there are illustrated two different ways in which two jawed instruments 312 and 314 can be inserted into a cannula tube 316 and used together in a procedure. In such instances, the jawed instruments 312 and 314 are separated from one another at the distal tip of the cannula tube 316. For example, in FIG. 41, the static inner shaft 322 is pinned or riveted to the holder 324 and the holder 324 pivots at this feature. The dynamic inner shaft 326 is also pinned or riveted to the holder 324. As the dynamic inner shaft 326 is moved linearly it will cause the holder 324 to rotate around its fixed, static pivot point. The two instruments 312 and 314 would be inserted into respective slots 332 and 334 on either end of the holder 324. Depending on how the holder 324 is pivoted, the two instruments 312 and 314 would either come together or be separated.

A cam operated separator 350 is shown in FIG. 41. In this case, after insertion by the user, the ramped or lobed separator 350 can be linearly extended beyond the outer cannula tube 316 using an elongated rod 352. There are two ramps or cam features on the separator 350. The two instruments 312 and 314 can be extended beyond the separator 350 and they will separate away from each other after moving against the separator ramps, like cam features. The separator 350 could include scallops so that as the two instruments 312 and 314 extend past the separator 350 within one set of scallops. The separator 350 would be rotated 90 degrees until the second set of scallops engage the two instruments 312 and 314 and separate them.

While the laparoscopic hand instruments of the subject invention have been shown and described with reference to several preferred embodiments, those skilled in the art will readily appreciate that various changes and/or modifications may be made thereto without departing from the spirit and scope of the subject invention as defined by the appended claims.

What is claimed is:

1. A surgical instrument for use in laparoscopic surgical procedures, comprising:
   a) an elongated shaped outer shaft having a longitudinal axis extending therethrough, opposed proximal and distal end portions, and having a non-circular beam shaped cross-sectional configuration that includes opposed lateral supports joined integrally together by a central transverse interior web section, which extends along the longitudinal axis of the elongated shaped outer shaft;
   b) an end effector operatively associated with the distal end portion of the elongated shaped outer shaft and including a pair of cooperating jaw members configured for movement between open and closed positions;
   c) a proximal handle assembly operatively associated with the proximal end portion of the elongated shaped outer shaft and including a pivoting actuation handle; and
   d) an elongated actuation member extending through the elongated shaped outer shaft, between the opposed lateral supports thereof, from the proximal handle assembly to the end effector, the actuation member having a longitudinal slot formed therein for accommodating the central transverse interior web section of the elongated shaped outer shaft, whereby movement of the actuation handle causes corresponding axial movement of the elongated actuation member relative to the central transverse interior web section of the elongated shaped outer shaft, resulting in movement of the cooperating jaw members.

2. A surgical instrument as recited in claim 1, wherein the distal end portion of the outer shaft includes a bifurcated yoke section for accommodating the cooperating jaw members of the end effector.

3. A surgical instrument as recited in claim 2, wherein the cooperating jaw members of the end effector are located inside of the bifurcated yoke section.

4. A surgical instrument as recited in claim 2, wherein the cooperating jaw members of the end effector are located outside of the bifurcated yoke section.

5. A surgical instrument as recited in claim 1, wherein a distal end portion of the actuation member is operatively connected to the cooperating jaw members of the end effector by a transverse cam pin.

6. A surgical instrument as recited in claim 5, wherein the transverse cam pin travels within linear slots formed in the bifurcated yoke section of the elongated shaped outer shaft and within an angled cam slot formed in each of the jaw members.

7. A surgical instrument as recited in claim 1, wherein a proximal end portion of the actuation member includes a coupling for operatively connecting the actuation member to the pivoting actuation handle.

8. A surgical instrument as recited in claim 1, wherein a proximal end portion of the actuation member includes flexible tabs for operatively connecting the actuation member to the pivoting actuation handle.

9. A surgical instrument as recited in claim 8, wherein the proximal end portion of the actuation member is cooperatively connected to an electrical contact pin for electrocautery tasks.

10. A surgical instrument as recited in claim 1, wherein the elongated shaped outer shaft has opposed concave lateral supports.

11. A surgical instrument as recited in claim 10, wherein the opposed concave lateral supports of the elongated shaped outer shaft have a generally rectangular configuration.

12. A surgical instrument as recited in claim 10, wherein the opposed concave lateral supports of the elongated shaped outer shaft have a generally rounded configuration.

13. A surgical instrument as recited in claim 1, wherein the elongated shaped outer shaft and the actuation member are adapted and configured for cooperative axial rotation relative to the handle assembly.

14. A surgical instrument for use in laparoscopic surgical procedures, comprising:
   a) an elongated shaped outer shaft having a longitudinal axis extending therethrough, opposed proximal and distal end portions, and having a non-circular beam shaped cross-sectional configuration that includes opposed concave lateral supports joined integrally together by a central transverse interior web section, which extends along the longitudinal axis of the elongated shaped outer shaft, wherein the opposed concave lateral supports have a generally rectangular configuration;
   b) an end effector operatively associated with the distal end portion of the elongated shaped outer shaft and including a pair of cooperating jaw members configured for movement between open and closed positions;
   c) a proximal handle assembly operatively associated with the proximal end portion of the elongated shaped outer shaft and including a pivoting actuation handle;
   d) an elongated actuation member extending through the elongated shaped outer shaft, between the opposed concave lateral supports, from the proximal handle assembly to the end effector, and having a longitudinal slot formed therein configured to accommodate the central transverse interior web section of the elongated shaped outer shaft, whereby movement of the actuation handle causes corresponding axial movement of the elongated actuation member relative to the central transverse interior web section of the elongated shaped outer shaft, resulting in movement of the cooperating jaw members.

15. A surgical instrument as recited in claim 14, wherein the distal end portion of the shaped shaft includes an integral bifurcated yoke section for accommodating the cooperating jaw members of the end effector.

16. A surgical instrument as recited in claim 15, wherein the cooperating jaw members of the end effector are located inside of the integral bifurcated yoke section.

17. A surgical instrument as recited in claim 15, wherein the cooperating jaw members of the end effector are located outside of the integral bifurcated yoke section.

18. A surgical instrument as recited in claim 14, wherein a distal end portion of the actuation member is operatively connected to the cooperating jaw members of the end effector by a transverse cam pin.

19. A surgical instrument as recited in claim 18, wherein the transverse cam pin travels within linear slots formed in the integral bifurcated yoke section of the elongated shaped shaft and within an angled cam slot formed in each of the jaw members.

20. A surgical instrument as recited in claim 14, wherein a proximal end portion of the actuation member includes a coupling for operatively connecting the actuation member to the pivoting actuation handle.

21. A surgical instrument as recited in claim 14, wherein a proximal end portion of the actuation member includes flexible tabs for operatively connecting the actuation member to the pivoting actuation handle.

22. A surgical instrument as recited in claim 21, wherein the proximal end portion of the actuation member is cooperatively connected to an electrical contact pin for electrocautery tasks.

23. A surgical instrument for use in laparoscopic surgical procedures, comprising:
   a) an elongated shaped outer shaft having a longitudinal axis extending therethrough, opposed proximal and distal end portions, and having a a non-circular beam shaped cross-sectional configuration that includes opposed concave lateral supports joined integrally together by a central transverse interior web section, which extends along the longitudinal axis of the elongated shaped outer shaft, wherein the opposed concave lateral supports have a generally rounded configuration;
   b) an end effector operatively associated with the distal end portion of the elongated shaped outer shaft and including a pair of cooperating jaw members configured for movement between open and closed positions;
   c) a proximal handle assembly operatively associated with the proximal end portion of the elongated shaped outer shaft and including a pivoting actuation handle;

d) an elongated actuation member extending within the elongated shaped outer shaft between the opposed concave lateral supports, from the proximal handle assembly to the end effector, and having a longitudinal slot formed therein configured to accommodate the central transverse interior web section of the elongated shaped outer shaft, whereby movement of the actuation handle causes corresponding axial movement of the elongated actuation member relative to the central transverse interior web section of the elongated shaped outer shaft, resulting in movement of the cooperating jaw members.

24. A surgical instrument as recited in claim 23, wherein the distal end portion of the shaped shaft includes an integral bifurcated yoke section for accommodating the cooperating jaw members of the end effector.

25. A surgical instrument as recited in claim 24, wherein the cooperating jaw members of the end effector are located inside of the integral bifurcated yoke section.

26. A surgical instrument as recited in claim 24, wherein the cooperating jaw members of the end effector are located outside of the integral bifurcated yoke section.

27. A surgical instrument as recited in claim 23, wherein a distal end portion of the actuation member is operatively connected to the cooperating jaw members of the end effector by a transverse cam pin.

28. A surgical instrument as recited in claim 27, wherein the transverse cam pin travels within linear slots formed in the integral bifurcated yoke section of the elongated shaped shaft and within an angled cam slot formed in each of the jaw members.

29. A surgical instrument as recited in claim 23, wherein a proximal end portion of the actuation member includes a coupling for operatively connecting the actuation member to the pivoting actuation handle.

30. A surgical instrument as recited in claim 23, wherein a proximal end portion of the actuation member includes flexible tabs for operatively connecting the actuation member to the pivoting actuation handle.

31. A surgical instrument as recited in claim 30, wherein the proximal end portion of the actuation member is cooperatively connected to an electrical contact pin for electrocautery tasks.

* * * * *